United States Patent [19]

Smith, Jr.

[11] Patent Number: 4,532,984

[45] Date of Patent: Aug. 6, 1985

[54] RAPID COOL AUTOCLAVE FURNACE

[75] Inventor: Charles W. Smith, Jr., Fairview, Pa.

[73] Assignee: Autoclave Engineers, Inc., Erie, Pa.

[21] Appl. No.: 618,930

[22] Filed: Jun. 11, 1984

[51] Int. Cl.³ .................. F25B 29/00; A21B 1/00; F27B 5/04

[52] U.S. Cl. ..................... 165/61; 219/400; 432/205

[58] Field of Search .......... 165/61; 219/400; 432/205

[56] References Cited

U.S. PATENT DOCUMENTS

4,349,333  9/1982  Bowles .................. 432/205

Primary Examiner—John J. Camby
Attorney, Agent, or Firm—Webb, Burden, Robinson & Webb

[57] ABSTRACT

An apparatus for gas pressure bonding, hot isostatic pressing or the like in which a workpiece may be treated at elevated temperatures and pressures comprises an elongate cylindrical pressure vessel for enclosing a furnace. The furnace comprises an insulated bottom and an insulated hood with openings near the top and bottom. The insulating hood rests upon the bottom for enclosing a workspace. Means for heating the workspace and means for cooling the pressure vessel are provided. The improvements according to this disclosure are means for establishing a first circulating flow of pressurized fluid down along the interior of the pressure vessel wall, means for establishing a second circulating flow of pressurized fluid down through the workspace. Heat exchange between the two circulating flows of pressurized fluid after the first flow has been cooled by flowing down along the interior wall of the pressure vessel and after the second flow has been heated by flowing down over the workpiece in the workspace provides for a unique temperature control in the workspace. The flow rate of at least one circulating flow of pressurized fluid is positively established by pumps or fans.

18 Claims, 5 Drawing Figures

RAPID COOL AUTOCLAVE FURNACE

BACKGROUND OF THE INVENTION

The problem of providing fast and uniform cooling of autoclave furnaces has been addressed repeatedly in the prior art for the reason that it is such a desirable objective. See, for example, U.S. Pat. Nos. 3,940,245; 4,022,446; 4,235,592; 4,246,957; 4,280,807; and 4,131,419.

Simply opening convection paths for the pressurized fluids along the interior wall of the pressure vessel increases the cooling rate but this approach has two decided drawbacks: the temperature distribution along the axis of the workpiece is often unacceptable since flow is entirely dependent upon the "buoyancy effect." Also, the fluids carried against the interior wall of the pressure vessel may be at the maximum vessel temperature when cooling commences. Notwithstanding the vessel walls are liquid cooled, the contact with pressurized fluids at the maximum temperature can be damaging to the vessel. Forced circulation during cooling within the workspace, that is, around the workpiece or workpieces, improves the temperature distribution along the axis of the workpiece but still allows the hottest pressurized fluids in the vessel to flow against the vessel wall.

It is an object of this invention to provide a rapid cooling autoclave furnace wherein multiple circulating flows of pressurized fluids within the vessel minimize the temperature differentials of the circulating fluids as they pass axially along the workpiece and to reduce the maximum temperature of the fluids along the inner wall of the pressurized vessel.

It should be understood that there are two types of temperature nonuniformity within the workspace or workpieces that are undesirable in an autoclave furnace. The first is the nonuniformity of the workspace or the workpieces along the vertical axis of the workspace. This is a result of the tendency of hotter fluids to rise in the vessel. This results in uneven thermal gradients from top to bottom in the furnace and workpieces. The second type of temperature nonuniformity is within the workpieces themselves. Due to heating or cooling of the surface of the workpieces faster than heat can be transferred into or out of the interior of the workpieces an inside-outside temperature gradient may develop.

The forced circulation of fluids within the workspace, as is taught in the prior art, helps to overcome the temperature gradient along the vertical axis of the workspace. It does so by redistributing the fluids so that the natural rise of the hotter fluids is controlled and directed. However, forced circulation can theoretically increase the inside-outside temperature gradients by increasing heating or cooling rates. It is an inescapable fact that the faster the heating or cooling of the workpieces, the greater the inside-outside temperature gradients. The challenge is to use circulation in the workspace in a way to promote top to bottom uniformity but also in a way not to cause undesirable inside-outside nonuniformity.

It is an object of applicants' invention to provide two circulating flows of pressurized fluid, one passing down along the inner wall of the pressure vessel for cooling the mass of fluid in that flow path and another passing down through the workspace to pick up heat from the workpiece or workpieces during cooling.

SUMMARY OF THE INVENTION

Briefly, according to this invention there is provided an apparatus for gas pressure bonding, hot isostatic pressing or the like in which the workpiece or workpieces may be treated at elevated temperatures and pressures. The apparatus comprises an elongate cylindrical pressure vessel for enclosing a furnace. The furnace comprises an insulated bottom and an insulated hood with openings near the top and bottom of the hood. The insulated hood rests upon the bottom for enclosing a workspace. Electrical heating elements are provided for supplying heat to the workspace. The pressure vessel wall has passages therein providing a continuous path for cooling fluid to be pumped through the vessel wall. If cooling loads permit, the continuous path for cooling fluid may be wrapped about the exterior of the pressure vessel wall. Fittings are arranged for connection to a source of pressurized fluid to fill the vessel therewith. Apparatus are provided for establishing a first circulating flow of pressurized fluid down along the interior of the pressure vessel wall. This apparatus comprises either a valve for metering the natural flow or a pump, preferably a variable speed constant displacement pump. At the beginning of the cooling mode the head provided by the buoyancy effect can actually cause a greater mass flow rate than desired in the first circulating flow. Hence, at this time the valve or pump restricts the natural flow of the pressurized fluid. Apparatus are provided for establishing a second circulating flow of pressurized fluid down through the workspace. This may comprise a fan at the base of the furnace, for example. There must exist a means for exchange of heat between the two circulating flows of pressurized fluid after the first flow has been cooled by flowing down along the interior wall of the pressure vessel wall and after the second flow has been heated by flowing down over the workpiece in the workspace. Preferably, there is a control for actively establishing the flow rate of at least one circulating flow of pressurized fluid. Hence, either or both the speed of the fan at the base of the furnace or the speed of the constant displacement pump at the base of the insulated hood should have a motor with a variable speed control.

According to one embodiment, the insulated furnace hood has openings near the top and bottom thereof. An open top cylindrical baffle rests inside the hood upon the bottom. Heating elements are mounted to the baffle or the inner wall of the hood. A fan is positioned in the bottom of the furnace for drawing fluids down inside the baffle and expelling them up between the outside of the baffle and the inside of the hood. A valve or constant displacement pump controls flow through openings in the bottom of the insulated hood such that during a heating mode, that is, when the workpiece is being heated, the valve or pump substantially prevents flow through the openings in the bottom of the hood and the fan is operated to cause flow around the baffle to promote temperature uniformity in the workspace. During a cooling mode, the valve or pump permits flow through the insulated hood whereby cooled fluid rises between the hood and the baffle and mixes with the hot fluids expelled between the baffle and the hood. The mixing of the fluids results in a heat exchange therebetween.

According to a most preferred embodiment, control devices control the heat exchange between the pressurized fluid circulating around the baffle, the pressurized fluid circulating around the hood and the cooling fluid in the wall of pressure vessel by adjusting the relative mass flow rates thereof.

According to another embodiment of this invention, in place of the above described open top baffle there is provided an inner heat conducting hood made of a suitable refractory metal resting upon the bottom of the furnace enclosing the workspace. The fan positioned in the bottom of the furnace draws fluid down within the workspace and expels it up along the inner wall of the inner hood. Hence, the circulation caused by the fan is mostly within the inner hood. The valve or pump associated with the openings in the insulated hood controls flow through openings in the bottom of the insulated hood. During a heating mode, no flow is permitted through the openings in the bottom of the hood while the fan is operated to cause flow around the workspace to promote temperature uniformity of the workspace. During a cooling mode, the valve or pump permits or causes flow through the insulated hood whereby cooled fluid rises between the insulated hood and the inner hood. Heat exchange takes place between the two flows or pressurized fluid rising along the sides of the heat conductive hood. In this embodiment heat must be transferred through the heat conducting hood.

A third embodiment according to this invention is similar to the first in that an open top cylindrical baffle rests inside the hood upon the bottom. A constant displacement pump draws pressurized fluid from between the insulated hood and the interior wall of the pressure vessel and injects it into a nozzle directed into the space between the inner hood and the insulated hood. The nozzle is arranged to draw pressurized fluid down through the workspace mixing it with fluid from the pump. During a heating mode, the constant displacement pump prevents flow through the openings in the bottom of the hood. At that time no action takes place in the nozzle. During a cooling mode, the constant displacement fan draws pressurized fluid through the hood and forces it into the nozzle. Cooled fluid rises between the inner hood and the baffle and mixes with the hot fluids drawn from the workspace. The fluids exchange heat upon mixing.

THE DRAWINGS

Further features and other objects and advantages will become apparent from the following detailed description made with reference to the drawings in which.

DESCRIPTION OF THE PREFERRED EMBODIMENTS

Figure 1:
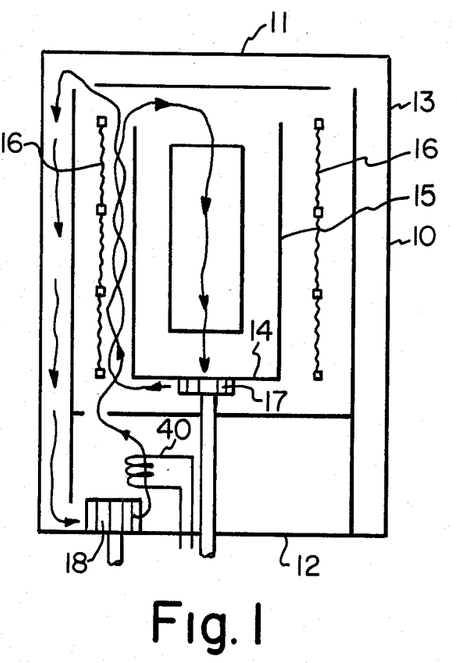
FIG. 1 is a schematic section view of an autoclave furnace according to this invention.

Referring to FIG. 1, there is shown an autoclave furnace having two pressurized fluid circulating flow paths during the cooling thereof. The autoclave furnace comprises a pressure vessel 10 having, for example, a cylindrical wall with a generally vertical axis. The cylindrical wall is fabricated of high strength steel and it is provided with a thickness enabling it to safely withstand the working pressures of the vessel. Typical working pressures for hot isostatic pressing are 2,000 to 25,000 psi. The pressure vessel has upper 11 and lower 12 end pieces at the axial ends. The end pieces are designed to form high pressure seals to the inner face of the cylindrical wall. The end pieces may be held in place by a number of devices, for example, by a reaction frame. See U.S. Pat. Nos. 4,155,476 and 4,126,757 for a description of a suitable pressure vessel for the practice of this invention. The details of the pressure vessel and the means for holding the end pieces in place form no part of this invention. Within the pressure vessel 10 is an insulated furnace hood 13. Upon a pedestal is a furnace hearth 14. Typically, the pedestal and furnace hearth 14 are spaced above the lower end piece 12 by a foot to provide a space for various utilities. See U.S. Pat. Nos. 4,247,755 and 4,268,708 for an illustration of furnace hoods used in autoclave furnaces.

The autoclave furnace is heated by electrical heating elements 16 positioned within the furnace hood. The heating elements may be refractory metal wires coiled and draped along the inner face of the insulated hood. They may also be mounted to an inner cylindrical baffle either inside or outside of the workspace. The heating elements may also be carbon or graphite or silicon carbide rods positioned along the walls or the workspace or positioned along a pedestal supporting a hearth space above the lower end piece. Typically, the electrical power is brought through the lower end piece of an autoclave furnace. The type of heating element and the location thereof is not critical to this invention. See U.S. Pat. Nos. 4,126,757 and 4,249,032 for an illustration of heating elements used in autoclave furnaces.

The ports that permit the interior of the vessel to be pressurized usually are provided in the lower end piece. Typically, inert gases such as argon and helium are used as the pressurizing fluid. At the high pressures used they have a density and viscosity similar to water. The density of the pressurized fluids in the vessel may vary from ten to fifty pounds per cubic foot depending upon the temperature in the vessel. This large density difference results in a very pronounced buoyancy effect.

It is always necessary to cool the walls of the pressure vessel but it is especially necessary where the hot fluids of the furnace are drawn against the interior surface of the walls in order to speed cooling. The typical technique for cooling the vessel wall is to wrap it with coils that carry cooling fluid. It is preferable to provide a channel for the flow of cooling fluid close to the interior surface of the vessel. This may be achieved by placing a cylindrical jacket within the main wall of the vessel. The jacket has a spiral or vertical groove on the exterior surface. The groove and the interior surface of the main wall form a channel for the cooling fluid.

Referring again to FIG. 1, there is shown an inner cylindrical liner 15 resting upon the furnace hearth 14 spaced inwardly from the inner face of the insulating hood. Since this liner is directly adjacent to the workspace it must be constructed of refractory metal or other high temperature material. The inner cylindrical liner has an open top.

A first fan 17 is provided in the bottom of the furnace for drawing fluids down out of the workspace and expelling them out and up through the space between the inner liner and the insulated hood. A preferred fan and technique for magnetically driving the fan are shown in U.S. Pat. Nos. 4,151,400 and 4,235,592. However, in these patents it is taught to use the fan to draw fluids down along the outside of a liner and to expel them up into the workspace within a liner. The impeller must be inverted for use in this invention. It is necessary to provide the axial intake of the impeller facing the workspace and to provide radial channels under the surface of the hearth leading to the space between the inner liner and the insulating hood. The first fan thus has the ability to create a circulating flow of pressurized fluid down through the workspace and up along the outside of the inner liner.

The insulating hood 13 is provided with openings at the top and at the bottom to provide communication between the interior and exterior of the hood. As shown in FIG. 1, the openings in the bottom of the hood are controlled by a pump 18. Preferably, the pump is a constant displacement pump. It may be magnetically driven through the base of the vessel (through the lower end piece). It is also possible to use a variable displacement pump in series with a metering valve that may be controlled from the exterior of the pressure vessel. The point is that at the beginning of the cooling mode (and for that matter during the heating mode) the buoyancy effect must be prevented from creating a flow of circulating fluid along the vessel wall greater than desired. During the heating mode no such circulation is desired.

The operation of the embodiment illustrated in FIG. 1 during the cooling mode is as follows: A first circulating flow of pressurized fluid is established by the fan 17 in the base of the furnace. A second circulating flow is established by the constant displacement pump 18. The two flows come together and intermix in the space between the inner liner 15 and the insulating hood 13. The mass flow rates of the two flows can be balanced to achieve the desired temperature uniformity in the workspace and to limit the rate of heat flow through the wall of the pressure vessel. The flow rates are controlled by sizing the fan and the constant displacement pump and by adjusting the speeds thereof. For example, the weight of the load (the workpieces) is assumed and the surface area is assumed. The desired cooling rate is assumed. From this it may be calculated that a certain mass of fluid at a certain velocity must be moved through the workspace for a given top to bottom temperature. Now the mass flow required in the second circulating flow can be calculated. Roughly, the mass flow rate of the second flow times the temperature drop in the flow along the vessel wall must equal the mass flow rate of the first flow times the temperature rise in the flow from top to bottom of the workspace. Since the specific calculations depend upon the particular pressure vessel and particular load a certain amount of trial and error is required in the design of a particular system. However, it can be said that during cooling the mass flow rate of the first flow is typically three to seven times the mass flow rate of the second (outside) flow.

For an autoclave furnace under consideration, it was determined that the vessel wall could safely remove heat at a rate of 480 KW. The vessel wall has an ID of about 50 inches and a length of about 145 inches. For cooling a mass of 9,000 lbs. (5,000 lbs. of workpieces and 4,000 lbs. of furnace, etc.) from 2200° F. to 400° F. in 20 minutes the average cooling rate must be about 400 KW. Hence, the cooling rate through the vessel wall is not a limitation. However, this furnace when conventionally cooled would only cool at an average rate of about 250 KW, far below the 400 KW rate desired.

According to this invention, two loops or flows are created during cooling. The inner loop is created and controlled by an 18 inch fan at the base of the workpiece. Mass flow rates produced by this fan will exceed 60,000 lbs./hr. at 600 RPM. This circulation removes heat from the workpieces and various furnace parts. The actual heat removal rate depends upon the workpiece characteristic length, the heat transfer coefficient around the workpiece, fan speed (RPM) and gas circulation flow area and the thermophysical properties of the workpiece.

The outer circulation loop is provided by a positive displacement pump. It may be assumed that the temperature of the gas in the outer loop decreases from a high temperature (near operating temperature at the beginning of the cooling mode) at the top of the vessel to near room temperature (about 100° F.) at the bottom of the vessel.

For an inner loop mass flow rate of 60,000 lbs./hr. it was established that the outer loop flow rate would have to be nearly 20,000 lbs./hr.

The parameters used in establishing the relative flow rates were as follows:

| | |
|---|---|
| The mass flow rate (inner loop) | 60,000 lbs./hr. |
| Outside diameter of the hood | 50.5" |
| Inside diameter of the pressure vessel (liner) | 51" |
| Outside diameter of the liner | 54.5" |
| Temperature at the beginning of cooling cycle | 2200° F. |
| Temperature at the end of cooling cycle | 400° F. |
| Pressure at the beginning of cooling cycle | 15,000 psi |
| Pressure at the end of the cooling cycle | 5,000 psi |
| Height of the hood | 144" |
| Diameter of the workbasket (convection liner) | 44.5" |
| Percent of flow area open | Variable |
| Volume - area ratio of the workpiece | Variable |
| Total mass of the workpiece | Variable |
| Density of the workpiece material | 0.284 lb./in$^3$ |
| Specific heat of the workpiece material | 0.11 Btu/lb. F |

Figure 2:
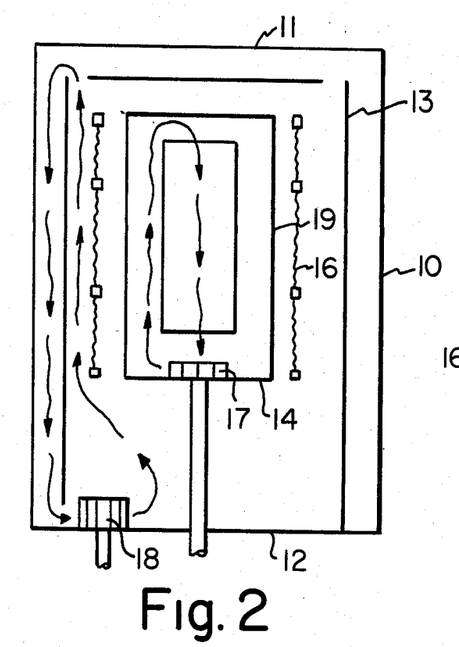
FIG. 2 is a schematic section view of an autoclave furnace according to a second embodiment of this invention.

Referring now to FIG. 2, there is illustrated another embodiment according to this invention. In this embodiment the open top inner liner is replaced with a heat conducting hood 19. The hood is substantially the liner with a closed top. The fan 17 in the bottom of the workspace draws one flow down through the workspace and expels it up along the inner surface of the heat conducting hood. The second circulating flow controlled by the constant displacement pump 18 works as in the above described embodiment. The significant difference between the embodiment of FIGS. 1 and 2 is that the two flows do not intermix and heat exchange between them is via the heat conducting hood. There are advantages for each embodiment. In the case of the embodiment of FIG. 1 heat transfer between flows is most efficient. In the case of the embodiment of FIG. 2 the temperature of the second (outer) flow entering the space between the insulated hood and the vessel wall is easier to control. In other words, the maximum temperature of the second flow can be kept lower and the minimum temperature of the first flow can be maintained higher because the two flows do not intermix. It should be understood that the heat conducting hood 19 of FIG. 2 does not seal out the surrounding furnace atmosphere as the pressure within must be substantially equal to the pressures without. Otherwise, the hood would collapse. The calculations to balance the mass flows of the first and second circulating flows of pressurized gas of the embodiment of FIG. 2 are very similar to those for the embodiment of FIG. 1.

Figure 3:
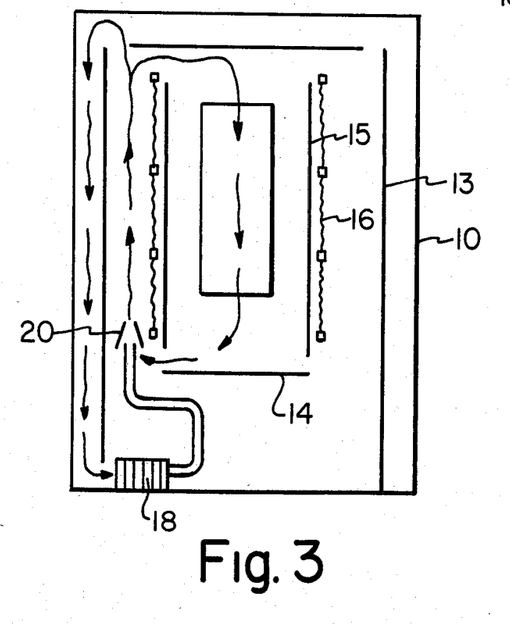
FIG. 3 is a schematic section view of an autoclave furnace according to a third embodiment of this invention.

Referring now to FIG. 3, there is illustrated a third embodiment according to this invention. This embodiment is similar to that of FIG. 1 in that there is an open top inner liner and the two flows intermix. The essential difference is that there is no fan in the furnace bottom. The output of the constant displacement pump 18 is forced into the nozzle 20 that delivers its output into the space between the inner liner and the insulating hood. The suction caused by the flow through the nozzle draws the first (inside) flow down through the workspace. The advantage of this embodiment is that it only requires one mechanical drive through the lower end piece of the vessel. However, since the first flow is dependent on the second, there is no forced convection in the workspace except during cooling.

Figure 4:
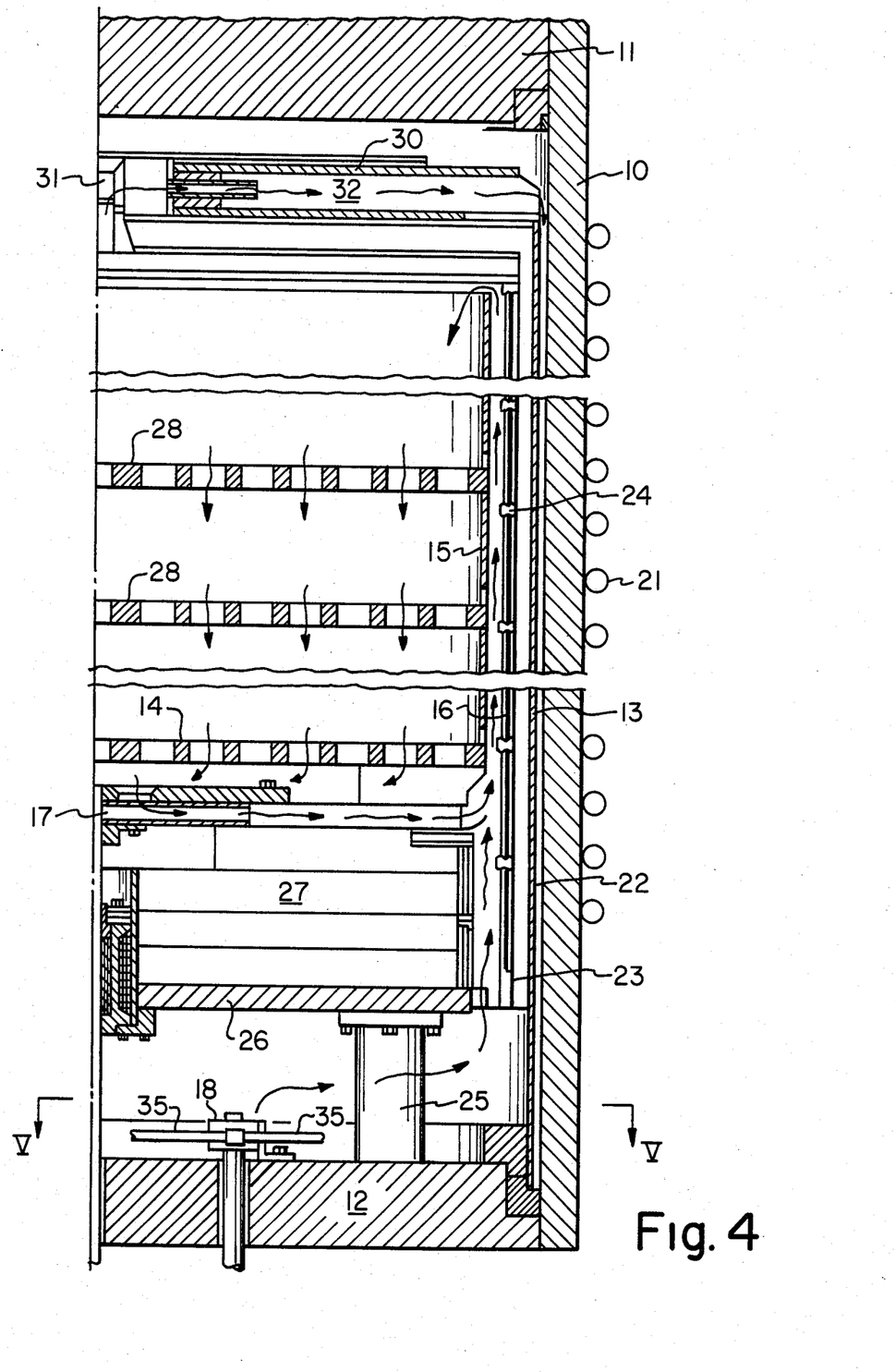
FIG. 4 is an axial section view of one substantially symmetrical half of an autoclave furnace according to the embodiment shown in FIG. 1.

Referring now to FIG. 4, there is shown a section of an autoclave furnace for the practice of the invention already described with reference to FIG. 1. The same numerals are used to identify the same elements in both drawings. The pressure vessel wall 10 is wrapped with cooling coils 21 for removing heat from the vessel wall. The furnace hood 13 is comprised of an outer structural wall 22 which is radially spaced from the interior of the pressure vessel 10 by about 0.5 inch. This space allows the down flow of hot gases to be cooled against the vessel wall during the cooling mode. The furnace hood in the illustrated embodiment further includes an inner wall 23 having insulated posts 24 extending radially inward therefrom for supporting the electrical heating elements 16.

A plurality of standards 25 support a table 26 spaced from the lower end piece 12. Resting upon the table is a pedestal 27 comprising, for example, a plurality of refractory metal walls. Rising up through the center of the endpiece, the table 26 and pedestal 27 is a shaft for driving fan 17. The fan comprises a refractory metal impeller located in an impeller chamber just below the top surface of the pedestal. Outlet passages exit radially outward from the impeller chamber below the top surface of the pedestal. Spaced above the top surface of the pedestal is a perforate hearth 14. The space between the pedestal and the imperforate hearth comprises an intake plenum for the fan.

Surrounding the workspace is an inner liner 15 from which perforate shelves 28 are supported. Hence, furnace atmosphere can be drawn down through the workspace into the plenum, into the axial opening in the fan which opening faces the plenum, and can then be expelled out through the radial passages in the pedestal and up through the space between the inner liner and the furnace hood.

The hood has a cover 30 that has a centrally located opening 31. The cover has radial passages 32 extending out from the centrally located opening. Hence, during the cooling mode the hot furnace atmosphere is passed up through the centrally located opening and out the radial passages in the cover 30. The atmosphere can then pass down between the furnace hood and the pressure vessel wall.

Located in the space below the table 26 is a pump 18 which is driven by a shaft rising up through the lower end piece of the pressure vessel. Preferably, both the pump 18 and the fan 17 are magnetically driven as already explained.

Figure 5:
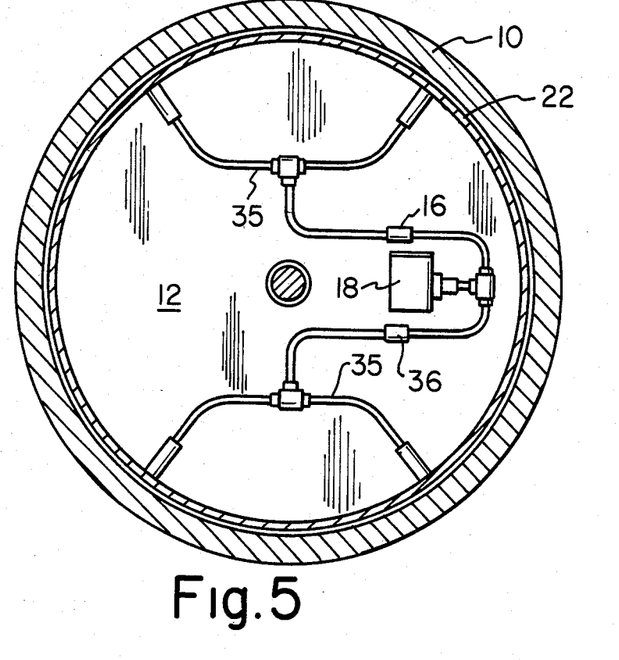
FIG. 5 is a radial section taken along line V—V of FIG. 4.

Referring to FIG. 5, at the base of the outer structural wall 22 of the furnace hood 13 there are a plurality of openings. The openings are joined together by conduits 35 and communicate with the intake to pump 18. According to a preferred embodiment, the conduits 35 have solenoid operated valves 36 positioned therein so that substantially no pressure is presented to the inlet of the pump 18 when the solenoid operated valves are closed.

During the cooling mode, the solenoid operated valves are opened and the pump 18 activated. Atmosphere from between the wall 22 and pressure vessel wall 10 is drawn through the conduits and expelled by the pump into the space below the table. The cooled atmosphere then flows up along the side of the pedestal and joins the flow of hot atmosphere being expelled from the radial passages in the top of the pedestal. The two flows mix and exchange heat in the space between the inner liner 15 and the furnace hood 13.

For unique situations where the rate of heat transfer through the vessel walls is still insufficient for the desired purposes, an auxiliary heat exchanger can be placed in the vessel in the space below the table. The heat exchanger may comprise a coiled conduit between inlet and outlet conduits 40 (see FIG. 1) passing through the lower end piece of the vessel for carrying cooling fluid. These conduits must be able to withstand the pressure of the vessel. The atmosphere emerging from the pump 18 is passed through the coiled conduit of the auxiliary heat exchanger to further cool the atmosphere flowing upward therefrom and to increase the rate of cooling of the workpiece.

While heat exchangers have been placed in autoclave furnaces before, they have been placed in line with a single circulating flow of the furnace atmosphere. The disadvantages of single flow cooling are not overcome. However, the double flow cooling pattern according to this invention gives increased advantage to the heat exchanger. The atmosphere reading the heat exchanger is not atmosphere at maximum temperature thus making materials design less difficult. Moreover, the atmosphere emerging from the heat exchanger is not directly applied to the workpieces thus facilitating vertical temperature uniformly during cooling.

Having thus described the invention in the detail and particularity required by the Patent Laws, what is desired protected by Letters Patent is set forth in the following claims.

I claim:

1. An apparatus for gas pressure bonding, hot isostatic pressing or the like in which a workpiece may be treated at elevated temperatures and pressures, said apparatus comprising a pressure vessel having an elongate cylindrical wall for enclosing a furnace; a furnace comprising an insulated bottom and an insulated hood with openings near the top and bottom thereof, said insulating hood resting upon the bottom for enclosing a workspace, means for heating the workspace, means for cooling the wall of the pressure vessel, means for establishing a first circulating flow of pressurized fluid down along the interior of the pressure vessel wall, means for establishing a second circulating flow of pressurized fluid down through the workspace, means for causing exchange of heat between the two circulating flows of pressurized fluid after the first flow has been cooled by flowing down along the interior wall of the pressure vessel and after the second flow has been heated by flowing down over the workpiece in the workspace, and means for positively establishing the flow rate of at least one circulating flow of pressurized fluid.

2. An apparatus for gas pressure bonding, hot isostatic pressing or the like in which a workpiece may be treated at elevated temperatures and pressures, said apparatus comprising a pressure vessel having an elongate cylindrical wall for enclosing a furnace, means for filling the vessel with pressurized fluids, means for cooling the wall of the pressure vessel, a furnace comprising an insulated bottom and an insulated hood with openings near the top and bottom thereof, said insulated hood resting upon the bottom for enclosing a workspace, an open top cylindrical baffle inside the hood resting upon the insulated bottom, electrical heating elements within the insulated hood, a fan positioned in the bottom of the furnace for creating a first flow by drawing fluids down inside the baffle and expelling them up between the hood and the outside of the baffle, means for controlling a second flow through openings in the bottom of the hood, such that during a heating mode the means for controlling flow prevents flow through the openings in the bottom of the hood and the fan can be operated to cause flow around the baffle to promote temperature uniformity of the workspace and such that during a cooling mode the means for controlling the second flow permits flow through the hood whereby cooled fluid rises between the hood and the baffle and mixes with the hot fluids of the first flow expelled between the baffle and the hood.

3. Apparatus according to claim 2 wherein the means for controlling comprise a positive displacement pump.

4. Apparatus according to claims 2 or 3 further comprising flow control means for controlling the heat exchange between the pressurized fluid circulating around the baffle, the pressurized fluid circulating around the hood and the means for cooling the pressure vessel by adjusting the mass flow rates thereof.

5. An apparatus for gas pressure bonding, hot isostatic pressing or the like in which a workpiece may be treated at elevated temperatures and pressures, said apparatus comprising a pressure vessel having an elongate cylindrical wall for enclosing a furnace, means for filling the vessel with pressurized fluids, means for cooling the wall of the pressure vessel, a furnace comprising an insulated bottom and an insulated hood with openings near the top and bottom thereof, said insulated hood resting upon the insulated bottom for enclosing a workspace, a heat conductive inner hood within the furnace enclosing the workspace, electrical heating elements within the insulated hood, a fan positioned in the bottom of the furnace for creating a first flow by drawing fluids down within the workspace and expelling them up along the inner wall of the inner hood, means for controlling a second flow through openings in the bottom of the insulated hood, such that during a heating mode the means for controlling the second flow prevents flow through the openings in the bottom of the insulated hood and the fan can be operated to cause flow around the workspace to promote temperature uniformity of the workspace and such that during a cooling mode the means for controlling flow permits flow through the insulated hood whereby cooled fluid rises outside of the workspace between the insulated hood and the inner hood heat transfer takes place between the first and second flows through the heat conductive inner hood.

6. Apparatus according to claim 5 wherein the means for controlling comprise a positive displacement pump.

7. Apparatus according to claims 5 or 6 further comprising flow control means for controlling the heat exchange between the pressurized fluid circulating within the inner hood and the pressurized fluid circulating around the insulated hood and the means for cooling the pressure vessel by adjusting the mass flow rates thereof.

8. An apparatus for gas pressure bonding, hot isostatic pressing or the like in which a workpiece may be treated at elevated temperatures and pressures, said apparatus comprising a pressure vessel having an elongate cylindrical wall for enclosing a furnace, means for filling the vessel with pressurized fluids, means for cooling the wall of the pressure vessel, a furnace comprising an insulated bottom and an insulated hood with openings near the top and bottom thereof, said insulated hood resting upon the insulated bottom for enclosing a workspace, an open top cylindrical baffle inside the hood resting upon the bottom, electrical heating elements within the insulated hood, a nozzle positioned to create a first flow by drawing fluid from the workspace and deliver fluid to the space between the baffle and insulated hood, a constant displacement pump for creating a second flow by drawing pressurized fluid from between the insulated hood and the interior wall of the pressure vessel and injecting it through said nozzle into the space between the inner hood and the insulated hood, such that during a heating mode the constant displacement pump prevents flow through the openings in the bottom of the hood, and such that during a cooling mode the constant displacement pump draws pressurized fluid through the hood whereby cooled fluid of the second flow rises between the inner hood and the baffle and mixes with the hot fluids of the second flow from the workspace in the nozzle.

9. Apparatus according to claim 8 further comprising flow control means for controlling the heat exchange between the pressurized fluid circulating around the baffle, the pressurized fluid circulating around the hood and the means for cooling the pressure vessel by adjusting the mass flow rates thereof.

10. Apparatus according to claims 1, 2, 5, 8, wherein an auxiliary heat exchanger is placed in the path of the second circulating flow.

11. Apparatus according to claim 1 wherein the means for positively establishing the flow rate comprises a positive displacement pump.

12. Apparatus according to claims 1 or 11 further comprising flow control means for controlling the heat exchange between the first circulating flow and the second circulating flow and the means for cooling the pressure vessel by adjusting the mass flow rates thereof.

13. An apparatus for gas pressure bonding, hot isostatic pressing or the like in which a workpiece may be treated at elevated temperatures and pressures, said apparatus comprising a pressure vessel having an elongate cylindrical wall with a generally vertical axis and upper and lower end pieces for enclosing a furnace, means for filling the vessel with pressurized fluids, means for cooling the wall of the pressure vessel, a furnace comprising an insulated bottom spaced above the lower end piece by a pedestal and an insulated hood with openings near the top and bottom thereof, said insulated hood resting upon the bottom for enclosing a workspace, an open top cylindrical refractory metal baffle inside the hood resting upon the insulated bottom, electrical heating elements within the insulated hood, an axial intake impeller fan positioned in the bottom of the furnace for creating a first flow by drawing fluids down inside the baffle and expelling them up between the hood and the outside of the baffle, means for controlling a second flow through openings in the bottom of the hood, such that during a heating mode the means for controlling flow prevents flow through the openings in the bottom of the hood and the fan can be operated to cause flow around the baffle to promote temperature uniformity of the workpiece and such that during a cooling mode the means for controlling the second flow permits flow though the hood such that cooled fluid rises between the hood and the baffle and mixes with the hot fluids of the first expelled between the baffle and the hood.

14. Apparatus according to claim 13 wherein the means for controlling comprise a positive displacement pump.

15. Apparatus according to claims 13 or 14 further comprising flow control means for controlling the heat exchange between the pressurized fluid circulating around the baffle, the pressurized fluid circulating around the hood and means for cooling the pressure vessel by adjusting the mass flow rates thereof such that the mass flow rate of the second flow times the temperature drop along the vessel wall substantially equals the mass flow rate of the first flow times the temperature rise moving down through the workspace.

16. An apparatus for gas pressure bonding, hot isostatic pressing or the like in which a workpiece may be treated at elevated temperatures and pressures, said apparatus comprising a pressure vessel having an elongate cylindrical wall with a generally vertical axis and upper and lower end pieces for enclosing a furnace, means for filling the vessel with pressurized fluids, means for cooling the wall of the pressure vessel, a furnace comprising an insulated bottom and an insulated hood with openings near the top and bottom thereof, said insulated hood resting upon the insulated bottom spaced above the lower end piece by a pedestal for enclosing a workspace, a refractory metal heat conductive inner hood within the furnace enclosing the workspace, electrical heating elements within the insulated hood, a fan positioned in the bottom of the furnace for creating a first flow drawing fluids down within the workspace and expelling them up along the inner wall of the inner hood, means for controlling a second flow through openings in the bottom of the insulated hood, such that during a heating mode the means for controlling the second flow prevents flow through the openings in the bottom of the insulated hood and the fan can be operated to cause flow around the workspace to promote temperature uniformity of the workspace and such that during a cooling mode the means for controlling flow permits flow through the insulated hood whereby cooled fluid rises outside the workspace between the insulated hood and the inner hood heat transfer takes place between the first and second flows through the heat conductive inner hood.

17. Apparatus according to claim 16 wherein the means for controlling comprise a positive displacement pump.

18. Apparatus according to claims 16 or 17 further comprising flow control means for controlling the heat exchange between the pressurized fluid circulating within the inner hood and the pressurized fluid circulating around the insulated hood and the means for cooling the pressure vessel by adjusting the mass flow rates thereof such that the mass flow rate of the second flow times the temperature drop along the vessel wall substantially equals the mass flow rate of the first flow times the temperature rise moving down through the workspace.

* * * * *

UNITED STATES PATENT AND TRADEMARK OFFICE
CERTIFICATE OF CORRECTION

PATENT NO. : 4,532,984

DATED : August 6, 1985

INVENTOR(S) : Charles W. Smith, Jr.

It is certified that error appears in the above-identified patent and that said Letters Patent is hereby corrected as shown below:

Claim 13 - Column 11 Line 9 "workpiece" should read --workspace--.

Signed and Sealed this

Twelfth Day of November 1985

[SEAL]

Attest:

DONALD J. QUIGG

Attesting Officer

Commissioner of Patents and Trademarks